United States Patent
Flachsmann et al.

(10) Patent No.: US 11,965,202 B2
(45) Date of Patent: Apr. 23, 2024

(54) METHOD OF MAKING 2-OXYGENATED DECALINS FROM ISOPRENOIDS USING A SQUALENE-HOPENE CYCLASE

(71) Applicant: GIVAUDAN SA, Vernier (CH)

(72) Inventors: Felix Flachsmann, Duebendorf (CH); Eric Eichhorn, Zurich (CH)

(73) Assignee: GIVAUDAN SA, Vernier (CH)

( * ) Notice: Subject to any disclaimer, the term of this patent is extended or adjusted under 35 U.S.C. 154(b) by 53 days.

(21) Appl. No.: 17/427,171

(22) PCT Filed: Feb. 26, 2020

(86) PCT No.: PCT/EP2020/054981
§ 371 (c)(1),
(2) Date: Jul. 30, 2021

(87) PCT Pub. No.: WO2020/173977
PCT Pub. Date: Sep. 3, 2020

(65) Prior Publication Data
US 2022/0127650 A1     Apr. 28, 2022

(30) Foreign Application Priority Data
Feb. 27, 2019   (GB) ..................................... 1902646

(51) Int. Cl.
C12P 7/02       (2006.01)
C12N 9/90       (2006.01)
C12P 7/26       (2006.01)
C12P 7/62       (2022.01)

(52) U.S. Cl.
CPC ..................................... *C12P 7/62* (2013.01)

(58) Field of Classification Search
None
See application file for complete search history.

(56) References Cited

U.S. PATENT DOCUMENTS 3,928,246 A    12/1975   Stadler et al.
5,386,039 A    1/1995    Snowden et al.

FOREIGN PATENT DOCUMENTS

| DE | 1811289 A1 | 7/1969 |
| DE | 1817918 A1 | 10/1973 |
| GB | 1209398 A | 10/1970 |
| WO | 2010139719 A2 | 12/2010 |
| WO | 2016091699 A1 | 6/2016 |
| WO | WO-2016170099 A1 * | 10/2016 ........... C07D 307/92 |

OTHER PUBLICATIONS

Hoshino et al., "Enzymatic cyclization reactions of geraniol, farnesol and geranylgeraniol, and those of truncated squalene analogs having C20 and C25 by recombinant squalene cyclase", Org. Biomol. Chem. 2:2650-2657, 2004 (Year: 2004).*

International Search Report and Written Opinion of the International Searching Authority for corresponding application PCT/EP2020/054981 dated May 11, 2020.

A. Gautier, et al.: "Preparation and Odor Evaluation of Both Enantiomers of 3,4,4a[alpha],5,6,7,8,8a[beta]-Octahydro-5,5,8a[beta]-trimethyl-2(1H)-naphthalenone and 1,2[alpha],3,4,4a[beta],5,6,7,8,8a[beta]-Decahydro-5,5,8a[beta]-trimethyl-2[beta]-na phthalenyl Acetate, Four Woody Odorants", Helvetica Chimica Acta, vol. 70, No. 8, 1987, pp. 2039-2044.

GB Search Report for corresponding application GB 1902646.7 dated Aug. 16, 2019.

Ochs, et al.;"Properties of purified squalene-hopene cyclase from Bacillus acidocaldarius", Eur. J. Biochem., 1990, 194 (1), pp. 75-80.

Seitz, M.,: "Characterization of the substrate specificity of squalene-hopene cyclases (SHCs)", (available at https://elib.uni-stuttgart.de/handle/11682/1400), 2012.

Vial, et al.,: "Structure-Activity Relationship in Ambergris-Type Woody Odorants Possessing a Hydronaphthalene Skeleton", Helv. Chim. Acta, 1989, 72, 1390-1399.

Eichhorn, E., et al.: "Biocatalytic Process for (−)-Ambrox Production Using Squalene Hopene Cyclase", Adv. Synth Catal., 360, 2339-2351 (2018).

* cited by examiner

Primary Examiner — David Steadman
(74) Attorney, Agent, or Firm — Curatolo Sidoti & Trillis Co., LPA; Floyd Trillis, III; Salvatore A. Sidoti

(57) ABSTRACT

A method for making 2-oxygenated decalins, and products thereof.

9 Claims, No Drawings

METHOD OF MAKING 2-OXYGENATED DECALINS FROM ISOPRENOIDS USING A SQUALENE-HOPENE CYCLASE

TECHNICAL FIELD

The present invention relates generally to methods for making 2-oxygenated decalins of formula (I). The present invention further relates to methods for making further compounds derived from the 2-oxygenated decalins of formula (I). The present invention also relates to the intermediate products and products of these methods, and the uses of said products.

BACKGROUND 2-oxygenated decalins may be used as fragrance molecules and/or may be intermediates in the synthesis of fragrance molecules. 2-Oxygenated decalins are currently synthesized from linear precursors via cyclization methods that require harsh, highly acidic conditions. Such conditions generally lead to mixtures of stereoisomeric and/or regioisomeric products. It is therefore desirable to provide alternative and/or improved methods for making 2-oxygenated decalins, for example that may require milder conditions and/or that allow for better control of the stereoisomers and/or regioisomers that are produced.

SUMMARY OF THE INVENTION

In accordance with a first aspect of the present invention there is provided a method for making a compound of formula (I)

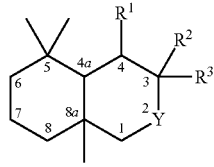

(I)

wherein Y is selected from CHOH and C=O,
$R^1$ and $R^2$ are independently selected from hydrogen, alkyl and cycloalkyl, and
$R_3$ is hydrogen or alkyl;
and wherein the method comprises contacting a compound of formula (II) with a squalene-hopene cyclase (SHC),

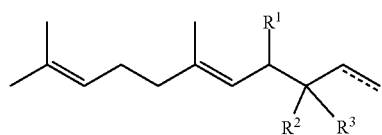

(II)

wherein $R^1$, $R^2$ and $R^3$ have the same meaning as for formula (I), and the dotted line represents together with the carbon-carbon bond either a double bond or a triple bond.

In accordance with a second aspect of the present invention there is provided a compound of formula (I). In certain embodiments, the compound of formula (I) is obtained by and/or obtainable by the method of the first aspect of the present invention.

In accordance with a third aspect of the present invention there is provided the use of a compound of formula (I) as a fragrance ingredient. In certain embodiments, the compound of formula (I) is obtained by and/or obtainable by the method of the first aspect of the present invention.

In accordance with a fourth aspect of the present invention there is provided a fragrance composition comprising one or more compound(s) of formula (I). In certain embodiments, one or more of the compound(s) of formula (I) is/are obtained by and/or obtainable by the method of the first aspect of the present invention.

In certain embodiments of any aspect of the present invention, $R_1$, $R_2$ and $R_3$ are hydrogen. In certain embodiments of any aspect of the present invention, $R_1$ and $R_2$ are hydrogen and $R_3$ is alkyl (e.g. methyl or ethyl) or cycloalkyl. In certain embodiments of any aspect of the present invention, $R_1$ is alkyl or cycloalkyl and $R_2$ and $R_3$ are hydrogen. In certain embodiments of any aspect of the present invention, $R_1$ is methyl and $R_2$ and $R_3$ are hydrogen. In certain embodiments of any aspect of the present invention, $R_1$ and $R_2$ are hydrogen and $R_3$ is cyclopropyl. In certain embodiments of any aspect of the present invention, $R_1$ and $R_2$ are alkyl (e.g. methyl or ethyl) and $R_3$ is hydrogen. In certain embodiments of any aspect of the present invention, $R_1$ is hydrogen and $R_2$ and $R_3$ are alkyl (e.g. methyl).

In certain embodiments of any aspect of the present invention, the SHC is an *Alicyclobacillus* SHC. In certain embodiments, the SHC is an *Alicyclobacillus acidocaldarius* (Aac) SHC. In certain embodiments, the SHC is a *Zymomonas mobilis* SHC.

In certain embodiments of any aspect of the present invention, the compound of formula (I) has an enantiomeric excess of at least about 95% of 4aS.

In certain embodiments of any aspect of the present invention, the method further comprises further reacting the compound of formula (I). In certain embodiments, the method further comprises oxidizing or dehydrating or esterifying the compound of formula (I).

Certain embodiments of any aspect of the present invention may provide one or more of the following advantages:
  milder reaction conditions (e.g. less acidic and/or corrosive reagents, lower temperature);
  products with higher regioisomeric and diastereomeric purity;
  optically active products;
  good product yield.

The details, examples and preferences provided in relation to any particulate one or more of the stated aspects of the present invention will be further described herein and apply equally to all aspects of the present invention. Any combination of the embodiments, examples and preferences described herein in all possible variations thereof is encompassed by the present invention unless otherwise indicated herein, or otherwise clearly contradicted by context.

DETAILED DESCRIPTION

The present invention is based, at least in part, on the surprising finding that squalene-hopene cyclases (SHCs) can be used to make 2-oxygenated decalins of formula (I) from compounds of formula (II). Without wishing to be bound by theory, it is thought that the reaction proceeds via the formation of a secondary or vinylic carbocation, which reacts with water to form a decalin alcohol or ketone, as depicted below.

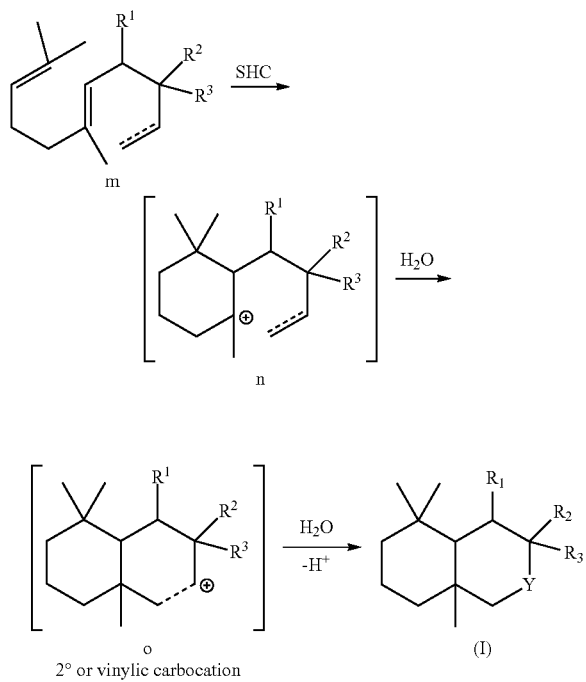

2° or vinylic carbocation

It is therefore particularly surprising that secondary decalin alcohols (i.e. compound of formula (I) wherein Y is CHOH) may be formed since secondary carbocations are generally less stable than tertiary carbocations. Likewise, it is particularly surprising that decalin ketones (i.e. compounds of formula (I) wherein Y is C=O) may be formed from terminal acetylenic substrates since formation of a carbon-carbon bond between the terminal acetylene carbon atom and the tertiary carbocation (n) requires an unexpected change in geometry of the rigid linear acetylene moiety. Such cyclizations do generally not occur without the presence of strong and/or nucleophilic Brønstedt or Lewis acids.

The present invention is further based, at least in part, on the finding that SHCs can be used to make 2-oxygenated decalins of formula (I) with high optical purity and/or high regioisomeric purity and/or diastereomeric purity.

Thus, there is provided herein a method for making a compound of formula (I),

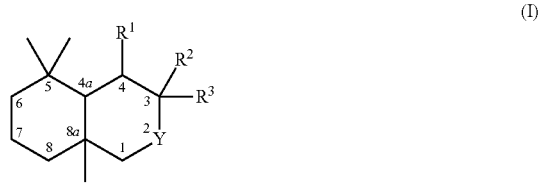

wherein Y is selected from CHOH and C=O,
R$^1$ and R$^2$ are independently selected from hydrogen, alkyl and cycloalkyl, and
R$_3$ is hydrogen or alkyl;
and wherein the method comprises contacting a compound of formula (II) with a squalene-hopene cyclase (SHC),

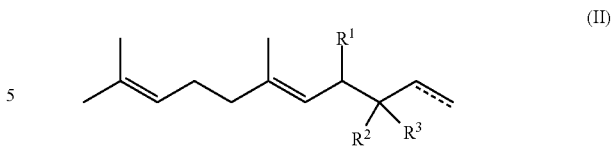

wherein R$^1$, R$^2$ and R$^3$ have the same meaning as for formula (I), and the dotted line represents together with carbon-carbon bond either a double bond or a triple bond.

The term "alkyl" refers to a linear straight chain or branched-chain saturated hydrocarbon group. The alkyl may, for example, have from 1 to 6 carbon atoms, for example from 1 to 5 carbon atoms, for example from 1 to 4 carbon atoms, for example from 1 to 3 carbon atoms, for example 1 or 2 carbon atoms. For example, the alkyl may be methyl, ethyl, propyl, butyl, iso-propyl or sec-butyl. For example, if R$^1$ is alkyl, the alkyl may be methyl or ethyl. For example, if R$^2$ and/or R$^3$ is alkyl, the alkyl may be methyl, ethyl or propyl.

The term "cycloalkyl" refers to a cyclic hydrocarbon group, which may optionally contain one double bond and which may optionally be substituted with one or more alkyl groups (the term "alkyl" being as defined above). The cycloalkyl may, for example, have from 3 to 7 carbon atoms, for example from 3 to 6 carbon atoms, for example from 3 to 5 carbon atoms. In certain embodiments, the cycloalkyl is a saturated cyclic hydrocarbon group. For example, the cycloalkyl may be cyclopropyl, cyclopentyl, cyclohexyl, or cycloheptyl (optionally substituted with an alkyl group, for example 2-methyl-cyclopent-1-yl, or 1-methyl-cyclohex-1-en-4-yl). In certain embodiments, the cycloalkyl is substituted with one or more (including 2, 3 or 4) alkyl groups having from 1 to 6 carbon atoms, for example one or more alkyl groups having 1 or 2 carbon atoms.

In certain embodiments of any aspect of the present invention, R$_1$, R$_2$ and R$_3$ are hydrogen. In certain embodiments of any aspect of the present invention, R$_1$ and R$_2$ are hydrogen and R$_3$ is alkyl (e.g. methyl or ethyl) or cycloalkyl. In certain embodiments of any aspect of the present invention, R$_1$ is alkyl or cycloalkyl and R$_2$ and R$_3$ are hydrogen. In certain embodiments of any aspect of the present invention, R$_1$ is methyl and R$_2$ and R$_3$ are hydrogen. In certain embodiments of any aspect of the present invention, R$_1$ and R$_2$ are hydrogen and R$_3$ is cyclopropyl. In certain embodiments of any aspect of the present invention, R$_1$ and R$_2$ are alkyl (e.g. methyl or ethyl) and R$_3$ is hydrogen. In certain embodiments of any aspect of the present invention, R$_1$ is hydrogen and R$_2$ and R$_3$ are alkyl (e.g. methyl).

The compound of formula (II) may, for example, be obtained commercially. Alternatively, products of formula (II) may be synthesized by carbon-carbon bond formation between an allyl halide or allyl ester or carbonate (V) and an allyl or alkinyl halide (VI) in the presence of a metal, such as magnesium, in a solvent, such as tetrahydrofurane or diethyl ether, and, optionally, in the presence of an additive, such as LiCuCl$_4$ for example as shown below.

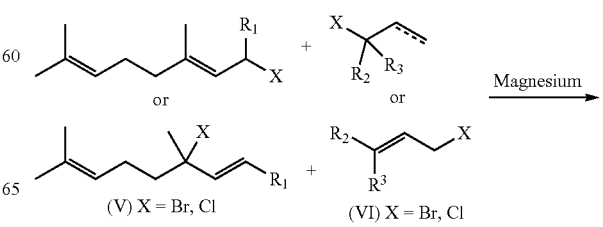

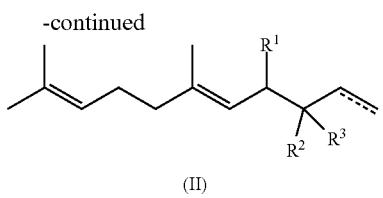

(II)

Alternatively, the compound of formula (II) containing a terminal alkene (i.e. wherein the dotted line together with the carbon-carbon bond represents a double bond) may be synthesized by an olefination reaction, for example a Wittig reaction between a carbonyl product (III) and a phosphonium salt (IV) in a solvent, such as tetrahydrofurane, and in the presence of a base, such as butyl lithium, at a temperature between −20° C. and +100° C., as shown below.

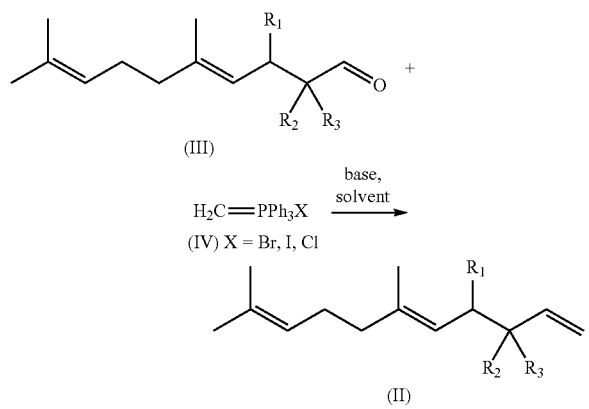

Workup and extraction of the thus formed products of formula (II) are known to the person skilled in the art. Products of formula (II) may be used in crude form or purified by known methods, such as distillation under reduced pressure and/or column chromatography on silica gel Alternatively, a product of formula (II) containing a terminal alkyne may be obtained from aldehyde (III) by a Corey-Fuchs reaction as shown in the example below.

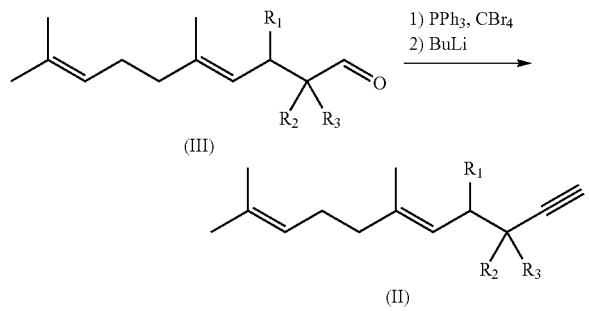

Compounds of formula (I) contain up to 4 chiral carbon atoms and thus can exist in the form of one or several stereoisomers, comprising enantiomers and diastereomers. The ratio of stereoisomers obtained may depend on the E/Z ratio of the compound of formula (II).

The method provided herein may be a method for stereoselectively synthesizing compounds of formula (I) from compounds of formula (II). This means that a given geometric isomer of the compound of formula (II) is converted to a single enantiomer of the compound of formula (I). The reaction may provide, for example, selectively the (4aS)-enantiomer from the 6-E-isomer of the product of formula (I).

The compound of formula (I) may comprise an enantiomeric excess of either the (4aR)-enantiomer or the (4aS)-enantiomer. The compound of formula (I) made by the methods described herein may, for example, have an enantiomeric excess of at least about 95% of 4aS (a compound of formula (Ia), wherein $R^1$, $R^2$, $R^3$ and Y have the same meaning as for formula (I)). For example, the compound of formula (I) may have an enantiomeric excess of at least about 96% or at least about 97% or at least about 98% or at least about 99% of 4aS. For example, the compound of formula (I) may have an enantiomeric excess up to about 100% of 4aS.

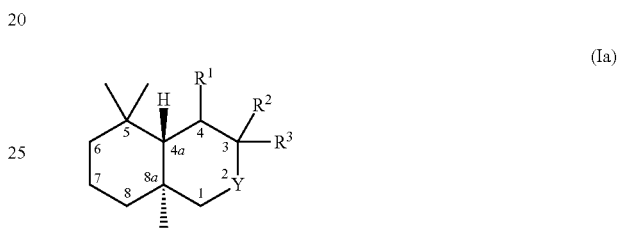

Enantiomeric excess (ee) is a measurement of the difference between the amounts of each enantiomer. For example, a mixture of 70% of one enantiomer and 30% of the other enantiomer has an enantiomeric excess of 40%. A racemic mixture has an enantiomeric excess of 0% and a completely pure enantiomer has an enantiomeric excess of 100%. The amount of each enantiomer in the mixture may, for example, be measured using methods such as gas chromatography on chiral columns and NMR spectroscopy in the presence of shift reagents.

Squalene-hopene cyclases (SHCs) are a group of enzymes that facilitate the conversion of an acyclic squalene molecule into the pentacyclic triterpenes hopene and hopanol, generally in a ratio of about 5:1. The SHC used in the presently provided methods may be of any type suitable for obtaining a compound of formula (I) from a compound of formula (II) as described herein and may be referred to as the SHC biocatalyst. The term SHC includes wild-type SHCs and variants of wild-type SHCs. The SHC may, for example, be selected from *Alicyclobacillus* SHC, *Bradyrhizobium* SHC (e.g. *Bradyrhizobium japonicum* SHC or *Bradyrhizobium diazoefficiens* SHC), *Methylococcus capsulatus* SHC, *Rhodopseudomonas palustris* SHC, *Streptomyces peucetius* SHC, *Streptomyces coelicolor* SHC, *Streptomyces scabiei* SHC, *Streptomyces sviceus* SHC, *Tetrahymena thermophila* SHC, *Geobacillus thermodenitrificans* SHC, *Thermosynechococcus elongatus* SHC, *Acidothermus cellulolyticus* SHC, *Catenulispora acidiphila* SHC, *Spherobacter thermophilus* SHC, *Saccharmomonospora viridis* SHC, *Teredinibacter turnerae* SHC, *Rhodopseudomonas palustris* SHC, *Acetobacter pasteurianus* SHC, *Syntrophobacter fumaroxidans* SHC and *Zymomonas mobilis* SHC. The SHC may, for example, be described in M. Seitz, "Characterization of the substrate specificity of squalene-hopene cyclases (SHCs)", Dissertation, University of Stuttgart (Germany), available at elib.uni-stuttgart.de/handle/11682/1400.

In certain embodiments, the SHC is an *Alicyclobacillus* SHC (said term including variants of *Alicyclobacillus* SHC), for example *Alicyclobacillus acidocaldarius* (Aac) SHC, *Alicyclobacillus herbarius* SHC, *Alicyclobacillus hesperidum* SHC, *Alicyclobacillus acidocaldarius* subsp. *rittmannii* or *Alicyclobacillus acidoterrestris* SHC. In certain embodiments, the SHC is an *Alicyclobacillus acidocaldarius* (Aac) SHC. The SHC (e.g. *Alicyclobacillus acidocaldarius* SHC) may, for example, be isolated from a natural source or may be produced from a recombinant microorganism. In certain embodiments, the SHC is a *Zymomonas mobilis* SHC. (e.g. *Zymomonas mobilis* SHC1).

SHC enzymes may also be defined by their function according to the EC classification. The Enzyme Commission number (EC number) is a numerical classification scheme for enzymes, based on the chemical reactions they catalyse. The SHC suitable for carrying out the reaction described herein belongs to the group of isomerases (EC 5) and may belong to the subgroup of intramolecular transferases (EC 5.4) transferring groups other than amino-, acyl-, phosphor-, or hydroxy (EC 5.4.99), *Alicyclobacillus acidocaldarius* SHC being member 5.4.99.17.

The SHC may, for example, be selected from one of the biocatalysts showing SHC activity as described in the Examples below, for example variant 215G2 of *Alicyclobacillus acidocaldarius* SHC—(mutations M132R, A224V, and 1432T).

The SHC may, for example, be isolated from nature or may be produced by recombinant gene expression. For example, *Alicyclobacillus acidocaldarius* SHC may be isolated from *Alicyclobacillus acidocaldarius* by the method described in Ochs et al., Eur. J. Biochem., 1990, 194(1), pages 75-80, the contents of which are incorporated herein by reference.

The methods described herein comprise contacting a compound of formula (II) with a SHC biocatalyst. The compound of formula (II) may, for example, be contacted with a cell producing the SHC or may be contacted with a cell extract comprising the SHC or may be contacted with the purified SHC, which may, for example, be immobilized on a support. The contacting of the compound of formula (II) and the SHC biocatalyst may, for example, require stirring or shaking.

The contacting of the compound of formula (II) and the SHC biocatalyst takes place under conditions suitable to convert the compound of formula (II) to the compound of formula (I). The contacting of the compound of formula (II) and the SHC biocatalyst may, for example, take place in an aqueous reaction medium, for example in a buffer. The conditions (e.g. temperature and pH) for the contacting of the compound of formula (II) and the SHC biocatalyst may, for example, be selected according to the optimal conditions of the SHC biocatalyst to be used in the reaction. The contacting of the compound of formula (II) and the SHC biocatalyst may, for example, take place in the presence of any species that assist the function of the SHC enzyme, for example a solubilizing agent, surfactant, or detergent such as sodium dodecyl sulfate or Triton X-100.

The compound of formula (II) and the SHC biocatalyst may be contacted at a temperature ranging from about 20° C. to about 60° C. For example, the compound of formula (II) and the SHC biocatalyst may be contacted at a temperature ranging from about 25° C. to about 60° C. or from about 30° C. to about 60° C. or from about 35° C. to about 60° C. or from about 40° C. to about 60° C. or from about 35° C. to about 55° C. or from about 40° C. to about 50° C.

The contacting of the compound of formula (II) with the SHC biocatalyst may, for example, take place at a pH ranging from about 4 to about 8. For example, the contacting of the compound of formula (II) with the SHC biocatalyst may take place at a pH ranging from about 5 to about 7 or from about 5.5 to about 7.5 or from about 6.5 to about 8.

The contacting of the compound of formula (II) with the SHC biocatalyst may, for example, take place for a period of time required to obtain a desired result. For example, the contacting of the compound of formula (II) with the SHC biocatalyst may take place for a period of time ranging from about 30 minutes to about 3 weeks. For example, the contacting of the compound of formula (II) with the SHC biocatalyst may take place for a period of time ranging from about 30 minutes to about 2 weeks or from about 30 minutes to about 1 week or from about 30 minutes to about 4 days or from about 30 minutes to about 3 days or from about 30 minutes to about 2 days or from about 30 minutes to about 24 hours or from about 1 hour to about 18 hours or from about 2 hours to about 16.

The compound of formula (II) and the SHC biocatalyst may be contacted in any amounts and in any proportion suitable to obtain the desired result in a desired period of time.

The concentration of the compound of formula (II) may, for example, range from about 0.5 g/l to about 500 g/l. For example, the concentration of the compound of formula (II) may range from about 1 g/l to about 250 g/l or from about 5 g/l to about 150 g/l or from about 15 g/l to about 100 g/l.

The required amount of SHC biocatalyst required for enabling sufficient conversion of the desired compound depends on the compound of formula (II). The concentration of the whole cells producing the SHC biocatalyst may, for example, range from about 5 g/l to about 500 g/l, for example from about 10 g/l to about 250 g/l, for example from about 15 g/l to about 150 g/l.

The method provided herein may, for example, result in the conversion of at least about 4% of the compound of formula (II). For example, the method may result in the conversion of at least about 10% or at least 20% or at least 30% or at least about 40% or at least about 50% of the compound of formula (II). The method provided herein may, for example, result in the conversion of up to about 100% or up to about 99% or up to about 98% or up to about 95% or up to about 90% of the compound of formula (II). The method may, for example, result in the conversion of from about 10% to about 100% or from about 20% to about 95% or from about 40% to about 90% or from about 25% to about 99% of the compound of formula (II).

The method provided herein may further comprise purification of the compound of formula (I) and/or separation from any unreacted compound of formula (II). For example, the compound of formula (I) may be purified by solvent extraction (e.g. using methyl-tert-butyl ether (MTBE) solvent) and/or distillation.

In certain embodiments, the compound of formula (I) wherein Y is CHOH may be further reacted. For example, the compound of formula (I) may be oxidized and/or may be dehydrated and/or may be esterified. For example, the compound of formula (I) may be converted to a ketone, a formate, an acetate, a propionate, a methyl carbonate, an ethyl carbonate or a N,N-dimethyl carbamate. For example, the compound of formula (I) may be dehydrated to form an olefin (alkene). The olefin (alkene) may then undergo acylation or epoxidation. The acylation or epoxidation may optionally be followed by rearrangement.

In certain embodiments, the compound of formula (I) wherein Y is C=O may be further reacted. For example, the carbonyl group of the compound of formula (I) may be reduced, for example by hydrogenation. The thus obtained compound may be acylated.

The method provided herein may further comprise purification of the product of the further reaction of the compound of formula (I) and/or separation from any unreacted compounds of formula (I) and/or formula (II). For example, the product may be purified by solvent extraction (e.g. using methyl-tert-butyl ether solvent), flash column chromatography on silica gel and/or distillation.

In certain embodiments, the method further comprises inverting the configuration of one of the formed stereocenters of formula (I), for example C(2). This may enhance a desired property of the final compounds, for example improve its odour strength and quality. The inversion may be effected by a suitable method known to the person skilled in the art, for example by an oxido-reduction or Mitsunobu reaction.

There is also provided herein the products of the methods described herein. For example, there is provided herein a product comprising a compound of formula (I). The compound of formula (I) may, for example, have an enantiomeric excess of at least about 95% of 4aS. For example, the compound of formula (I) may have an enantiomeric excess of at least about 96% or at least about 97% or at least about 98% or at least about 99% of 4aS. For example, the compound of formula (I) may have an enantiomeric excess up to about 100% of 4aS.

There is further provided herein the use of the products of the methods described herein as a fragrance. Thus, there is also provided herein a fragrance composition comprising one or more compounds of formula (I) and/or one or more products of further reacting a compound of formula (I) as described above.

By "fragrance composition" is meant any composition comprising one or more compounds of formula (I) and/or one or more products of further reacting a compound of formula (I) as described above, and a base material.

As used herein, the "base material" includes all known fragrance ingredients selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, diluents, and other auxiliary agents commonly used in the art.

Fragrance ingredients known to the art are readily available commercially from the major fragrance manufacturers. Non-limiting examples of such ingredients include:

essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;

alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,6Z)-3,7,11-trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl)pentan-2-ol); terpineol (2-(4-methylcyclohex-3-en-1-yl)propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;

aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl) ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl) ethanone); Isoraldeine® ((E)-3-methyl-4-(2,6,6-trimethylcyclohex-2-en-1-yl)but-3-en-2-one); 3-(4-isobutyl-2-methylphenyl)propanal; maltol; methyl cedryl ketone; methylionone; verbenone; and/or vanillin;

ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2',2',3,7,7-pentamethylspiro[bicyclo[4.1.0]heptane-2,5'-[1,3]dioxane]);

macrocycles, e.g. Ambrettolide ((Z)-oxacycloheptadec-10-en-2-one); ethylene brassylate (1,4-dioxacycloheptadecane-5,17-dione); and/or Exaltolide® (16-oxacyclohexadecan-1-one); and heterocycles, e.g. isobutylquinoline (2-isobutylquinoline).

As used herein, "carrier material" means a material which is practically neutral from an odorant point of view, i.e. a material that does not significantly alter the organoleptic properties of odorants.

By "diluents" is meant any diluent conventionally used in conjunction with odorants, such as diethyl phthalate (DEP), dipropylene glycol (DPG), pentane-1,2-diol, isopropyl myristate (IPM), triethyl citrate (TEC) and alcohol (e.g. ethanol).

The term "auxiliary agent" refers to ingredients that might be employed in a fragrance composition for reasons not specifically related to the olfactive performance of said composition. For example, an auxiliary agent may be an ingredient that acts as an aid to processing a fragrance ingredient or ingredients, or a composition containing said ingredient(s), or it may improve handling or storage of a fragrance ingredient or composition containing same, such as anti-oxidant adjuvant. Said anti-oxidant may be selected, for example, from Tinogard® TT (BASF), Tinogard® Q (BASF), Tocopherol (including its isomers, CAS 59-02-9; 364-49-8; 18920-62-2; 121854-78-2), 2,6-bis(1,1-dimethylethyl)-4-methylphenol (BHT, CAS 128-37-0) and related phenols, hydroquinones (CAS 121-31-9).

It might also be an ingredient that provides additional benefits such as imparting colour or texture. It might also be an ingredient that imparts light resistance or chemical stability to one or more ingredients contained in a fragrance composition.

A detailed description of the nature and type of auxiliary agent commonly used in fragrance compositions containing same cannot be exhaustive, but it has to be mentioned that said ingredients are well known to a person skilled in the art.

EXAMPLES

The biocatalyst (*Alicyclobacillus acidocaldarius* variant 215G2 (mutations M132R, A224V, and I432T)) was produced in *E. coli* as described in Eichhorn E., Locher E, Guillemer S., Wahler D., Fourage L., Schilling B., *Adv. Synth Catal.* 360, 2339-2351 (2018), the contents of which are incorporated herein by reference.

The approximate conversion was estimated from GC-FID of substrate and product peak area ratio according to the following equation:

$$\text{Approx. conversion} = 100 \times \text{Area}_{Product}/(\text{Area}_{Product} + \text{Area}_{substrate})$$

Example 1: SHC-Mediated Biotransformation of 6,10-dimethylundeca-1,5,9-triene to (2R,4aS,8aR)-5,5,8a-trimethyldecahydronaphthalen-2-ol 6,10-dimethylundeca-1,5,9-triene (5E/Z=61:39; prepared via Wittig-olefination of 5,9-dimethyldeca-4,8-dienal) was cyclized using *Alicyclobacillus acidocaldarius* variant 215G2 (mutations M132R, A224V, and I432T).

A typical cyclization reaction was run in a total volume of 150 g (Infors HT 0.75 l reactor) and contained 1.0 to 1.6 g 6,10-dimethylundeca-1,5,9-triene, 1.3% (w/v) Sodium Dodecyl Sulfate (SDS) and 250 g/l wet weight of cells, in 0.1 M succinic acid/NaOH buffer pH 5.4.

The reaction vessel was loaded with 6,10-dimethylundeca-1,5,9-triene. 1.95 g SDS was added from a 31% (w/w) aqueous solution. A cell suspension was prepared from *E. coli* cells that had produced the 215G2 SHC variant by suspending the cells in 0.1 M succinic acid/NaOH buffer pH 5.4. After determination of the cell wet weight of this suspension by centrifugation of an aliquot for 10 min at 10° C. and 17210 g, the volume of cell suspension for 37.5 g (250 g/l) wet weight of cells was added to the reaction vessel. The volume of the reaction was completed to 150 g with the required amount of reaction buffer. The reaction was run at 35° C. under constant stirring (700 rpm). pH was set to 5.4 using 85% phosphoric acid.

The reaction was sampled over time, the samples extracted with methyl-tert butyl ether (MTBE) and appropriately diluted for analyzing their content by GC-FID analysis: approx. 1 ml reaction was extracted with 4-5 ml MTBE. After centrifugation (tabletop centrifuge, 13000 rpm, 2 min) 0.1 ml solvent phase was diluted 1:5 in MTBE. 1 μl solvent phase was injected (split ratio 1/10) onto a 30 m×0.32 mm×0.25 μm Zebron ZB-5 GC column (Thermo Trace 1310 gas chromatograph). The column was developed at constant flow (4 ml/min $H_2$) with the following temperature gradient: 100° C., 15° C./min to 200° C., 120° C./min to 240° C., 4 min at 240° C. Inlet temperature: 200° C., detector temperature: 300° C. Conversion: approx. 26-45% in approximately 70-90 hours of reaction time.

A total of 7.5 g 6,10-dimethylundeca-1,5,9-triene was cyclized in 6 independent reactions. All reactions were finally pooled resulting in approximately 800 ml reaction broth. The reaction broth was extracted 4 times with 300 ml MTBE by vigorous shaking, followed by phase separation by centrifugation (Sorvall RC5B, GS3 rotor, 8000 rpm, 15 min). The solvent phases were recovered and GC-analyzed for their content after appropriate dilution in MTBE. 4 extractions allowed recovering 99% of the reaction product.

The crude MTBE-extract was dried and the residue filtered over a plug of silica gel, eluting with a gradient of 100% heptane to 100% MTBE. The fractions containing the product alcohol were pooled and further purified by flash chromatography on a silica gel cartridge with heptane/MTBE 3:1 to yield (2R,4aS,8aR)-5,5,8a-trimethyldecahydronaphthalen-2-ol (1.09 g) as a colourless liquid. The relative configuration was determined via 2D-NMR spectroscopy and the absolute configuration was determined on the ketone obtained after oxidation (see Example 2).

$^1$H-NMR ($CD_6D_6$, 600 MHz): 3.51-3.64 (m, 1H), 1.93 (br d, J=10.5 Hz, 1H), 1.49-1.59 (m, 1H), 1.46 (br d, J=10.9 Hz, 2H), 1.25-1.36 (m, 4H), 0.94-1.12 (m, 5H), 0.91 (t, J=11.5 Hz, 1H), 0.78 (d, J=14.7 Hz, 6H), 0.72 (s, 3H). $^{13}$C-NMR ($C_6D_6$, extracted from HSQC, 150 MHz): 66.5 (d), 54.4 (t), 52.9 (d), 42.3 (t), 42.0 (t), 37.1 (t), 34.9 (s), 33.0 (q), 32.8 (s), 21.0 (q), 20.8 (t), 19.7 (q), 18.5 (t).

MS (EI, 70 eV): 178 (11, $[M-H_2O]^+$), 163 (72), 149 (5), 137 (100), 122 (21), 107 (25), 95 (36), 81 (41), 69 (29), 55 (40), 41 (46), 29 (12).

Example 2: Preparation of (4aS,8aR)-5,5,8a-trimethyloctahydronaphthalen-2(1H)-one from (2R,4aS,8aR)-5,5,8a-trimethyldecahydronaphthalen-2-ol 2R,4aS,8aR)-5,5,8a-trimethyldecahydronaphthalen-2-ol (prepared in Example 1, 1.09 g, 5.55 mmol) was dissolved in acetone (40 mL) and the solution was cooled to 5° C. Jones-Reagent (1.38 mL) was added dropwise, upon which the colour turned green. The mixture was further stirred at room temperature for 1 h, then isopropanol was added (4 mL). The mixture was poured on 2 M aq. NaOH solution (100 mL), followed by extraction with MTBE. The combined organic layers were washed with water (100 mL) and diluted aq. NaCl-solution, then dried over $MgSO_4$ and concentrated. The crude product was purified by flash chromatography on a silica gel cartridge with heptane/MTBE 94:6 to yield (4aS,8aR)-5,5,8a-trimethyloctahydronaphthalen-2 (1H)-one (0.66 g, 61%) as a white crystalline solid.

Odour description (10% in DPG on paper blotter, 4 h): Woody, coniferous, green.

$[\alpha]_D = -82°$ (c=0.96, $CHCl_3$)

Enantiomeric excess>99.9% by chiral GC (25 m×0.25 mm Hydrodex-beta-3P, 1 μl injection volume (1000 ng/μl), split 20:1, injector 230° C., temperature program 2 min@50° C.-2° C./min-2 min@200° C., FID detection, (−)-isomer 48.7 min, (+)-isomer 49. 2 min).

$^1$H-NMR ($C_6D_6$, 600 MHz): 2.39-2.46 (m, 1H), 2.22-2.34 (m, 1H), 2.11-2.18 (m, 1H), 1.95-2.06 (m, 2H), 1.63 (s, 1H), 1.62-1.70 (m, 1H), 1.41-1.52 (m, 4H), 1.21-1.31 (m, 2H), 0.97 (s, 3H), 0.90 (br. s, 3H), 0.85 (s, 3H).

$^{13}$C-NMR ($C_6D_6$, extracted from HSQC, 150 MHz): 211.8 (s), 59.6 (t), 52.2 (d), 42.3 (t), 42.0 (t), 42.0 (t), 38.4 (s), 33.3 (s), 33.2 (q), 23.1 (t), 21.4 (q), 19.4 (q C), 18.8 (t).

MS (EI, 70 eV): 194 (48, $[M]^+$), 179 (34), 176 (24), 161 (59), 151 (17), 137 (54), 123 (72), 109 (90), 95 (100), 81 (64), 69 (81), 55 (79), 41 (85), 29 (19).

Example 3: Preparation of (4aS,8aR)-5,5,8a-trimethyloctahydronaphthalen-2(1H)-one from 6,10-dimethylundeca-5,9-dien-1-yne 6,10-dimethylundeca-5,9-dien-1-yne (5E/Z=72:28) was prepared via Corey-Fuchs reaction of Calmusal (5,9-Dimethyldeca-4,8-dienal). It was cyclized using *Alicyclobacillus acidocaldarius* variant 215G2 (mutations M132R, A224V, and I432T).

A typical reaction was run in 0.1 M succinic acid/NaOH buffer at pH 5.4. The reaction volume was 5 ml. The reaction contained 4 g/l 6,10-dimethylundeca-5,9-dien-1-yne (4

E/Z=72:28), 0.070% (w/v) Sodium Dodecyl Sulfate (SDS) and cells at an OD$_{650nm}$ of 40.0. The reactions were incubated at 35° C. on a Heidolph Synthesis 1 Liquid 24 device with constant agitation (900 rpm).

The reaction was sampled over time, the samples extracted with methyl-tert butyl ether (MTBE) and appropriately diluted for analyzing their content by GC-FID analysis: 0.2 ml reaction sample was extracted with 0.7 ml MTBE. After centrifugation (tabletop centrifuge, 13000 rpm, 2 min) was 1 µl solvent phase injected (split ratio 1/10) onto a 30 m×0.32 mm×0.25 µm Zebron ZB-5 GC column (Thermo Trace 1310 gas chromatograph). The column was developed at constant flow (4 ml/min H$_2$) with the following temperature gradient: 100° C., 15° C./min to 200° C., 120° C./min to 240° C., 4 min at 240° C. Inlet temperature: 200° C., detector temperature: 300° C.

A total of 20 mg 6,10-dimethylundeca-5,9-dien-1-yne was cyclized. After 24 hours of incubation were the reactions pooled and the resulting reaction broth extracted three times with 5 ml MTBE. The MTBE extract was evaporated to yield 11 mg of a viscous oil which was dissolved in CH$_2$Cl$_2$ and 60 mg of SiO$_2$ was added. The powder obtained after slow evaporation of the solvent was loaded onto a micro-flash chromatography column consisting of a Pasteur pipette equipped with a cotton plug and 500 mg of SiO$_2$ which had been preconditioned with hexane. Elution of the products was effected under a slight N$_2$-pressure with a gradient of hexane 100% to hexane/MTBE 1:1. The fractions eluting with hexane/MTBE 4:1 contained the product. They were combined and the solvent was evaporated. The residue was found to be identical to (4aS,8aR)-5,5,8a-trimethyloctahydronaphthalen-2(1H)-one obtained in Example 2 by 2D-NMR- and chiral GC-analysis.

Example 4: Preparation of (2S,4aS,8aR)-5,5,8a-trimethyldecahydronaphthalen-2-yl acetate from (4aS,8aR)-5,5,8a-trimethyloctahydronaphthalen-2(1H)-one In a stainless steel autoclave, (4aS,8aR)-5,5,8a-trimethyl-octahydronaphthalen-2(1H)-one (prepared in Example 2, 0.46 g, 2.4 mmol) was dissolved in acetic acid (20 mL) and PtO$_2$ (30 mg) was added. Hydrogenation was effected at room temperature and 4 bar H$_2$ pressure for 7 h. The mixture was poured into 2M aq. NaOH solution (40 mL), followed by extraction with methyl t-butyl ether. The combined organic layers were washed with water (40 mL) and diluted aq. NaCl-solution, then dried over MgSO$_4$ and concentrated.

The crude product was dissolved in cyclohexane (20 mL) and acetylated with acetyl chloride (0.52 g, 6.7 mmol, 2.8 equiv.) and pyridine (0.56 g, 7.0 mmol, 2.9 equiv.) at room temperature for 1 h, then at reflux for 3 h. The mixture was added to 2M aq. HCl solution (30 mL), followed by extraction with MTBE. The combined organic layers were washed with water (40 mL) and brine, then dried over MgSO$_4$ and concentrated. The crude was purified by flash column chromatography on a silica gel cartridge with heptane/MTBE 97:3 to yield (2S,4aS,8aR)-5,5,8a-trimethyldecahydronaphthalen-2-yl acetate (0.40 g, 70%, purity 98% according to GC-MS).

Odour description (10% in DPG on paper blotter, 4 h): woody, ambery, rich, diffusive.

[α]$_D$=−15° (c=0.54, CHCl$_3$)

Enantiomeric excess>99.9% by chiral GC (25 m×0.25 mm Hydrodex-beta-3P, 1 µl injection volume (1000 ng/µl), split 20:1, injector 230° C., temperature program 2 min@50° C.−1° C./min−2 min@190° C., FID detection, (−)-isomer 86.6 min, (+)-isomer 88. 2 min).

Enantiomeric excess (ee) is a measurement of the difference between the amounts of each enantiomer. For example, a mixture of 70% of one enantiomer and 30% of the other enantiomer has an enantiomeric excess of 40%. A racemic mixture has an enantiomeric excess of 0% and a completely pure enantiomer has an enantiomeric excess of 100%. The amount of each enantiomer in the mixture may, for example, be measured using methods such as chiral column chromatography and NMR spectroscopy.

It was found that this very pure (−)-enantiomer ((2S,4aS,8aR)-5,5,8a-trimethyl-decahydronaphthalen-2-yl acetate) is 6 times stronger (GC-threshold) than the pure (+)-enantiomer ((2R,4aR,8aS)-5,5,8a-trimethyl-decahydronaphthalen-2-yl acetate). This is surprising as several literature references point out that the (−)-enantiomer is less strong than the (+)-enantiomer (Gautier et al., Helv. Chim. Acta 1987, 70, 2039, describe (−)-enantiomer as less rich, and also Vial et al, Helv. Chim. Acta 1989, 72, 1390, describe racemic Polywood® (rac.-(2S,4aS,8aR)-5,5,8a-trimethyl-decahydronaphthalen-2-yl acetate) as "strong woody, very characteristic, dry and warm", whereas the pure (−)-isomer is described as only "woody, dry, amber like". Accordingly, the literature teaches that the (+)-isomer is preferred and stronger than the (−)-isomer.

$^1$H-NMR (CDCl$_3$, 400 MHz): 5.01 (quin, J=3.0 Hz, 1H), 2.03 (s, 3H), 1.90-1.98 (m, 1H), 1.33-1.72 (m, 8H), 1.27 (dd, J=14.7, 3.3 Hz, 1H), 1.14-1.23 (m, 1H), 1.04 (s, 3H), 0.90-1.01 (m, 2H), 0.87 (s, 3H), 0.83 (s, 3H).

$^{13}$C-NMR (CDCl$_3$, 100 MHz): 170.6 (s), 70.6 (d), 53.9 (d), 47.8 (t), 42.4 (t), 42.1 (t), 34.2 (s), 33.1 (q), 33.0 (s), 32.2 (t), 21.6 (q), 21.3 (q), 20.8 (q), 18.3 (t), 17.6 (t).

MS (EI, 70 eV): 178 (26, [M-AcOH]*), 163 (79), 149 (31), 135 (24), 124 (100), 109 (79), 93 (48), 81 (71), 67 (35), 55 (39), 43 (100), 29 (10).

The invention claimed is:
1. A method of making a compound of formula (I), wherein the method comprises the step of:
   contacting a compound of formula (II) with a squalene-hopene cyclase (SHC),

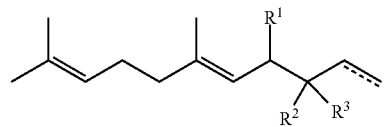

to produce a compound of formula (I)

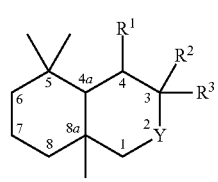

wherein Y of formula (I) is selected from CHOH and C=O,
wherein R$^1$, R$^2$ and R$^3$ are the same for formula (I) and formula (II) and the dotted line of formula (II) represents, together with the carbon-carbon bond, either a double bond or a triple bond, wherein $R^1$ and $R^2$ are independently selected from hydrogen, alkyl and cycloalkyl, wherein $R^3$ is hydrogen or alkyl, and wherein the SHC is variant 215G2 of *Alicyclobacillus acidocaldarius* SHC.

2. The method of claim 1, wherein $R^1$, $R^2$, and $R^3$ are hydrogen.

3. The method of claim 1, wherein the compound of formula (II) and the SHC are contacted at a pH ranging from 4 to 8.

4. The method of claim 1, wherein the compound of formula (I) is produced in an enantiomeric excess of at least 95% of 4aS.

5. The method of claim 1, wherein Y is CHOH and the method further comprises oxidizing, dehydrating or esterifying the CHOH, optionally followed by acylation or epoxidation of the oxidized, dehydrated or esterified CHOH.

6. The method of claim 1, wherein Y is C═O and the method further comprises reducing the C═O.

7. The method of claim 6, wherein the C═O is reduced by hydrogenation, optionally followed by acylation of the resulting secondary alcohol.

8. The method of claim 6, wherein $R^1$, $R^2$, and $R^3$ are hydrogen, wherein the C═O is reduced to CH—OH, and wherein the CH—OH is acetylated to —CH—O—C(O)CH$_3$.

9. The method of claim 7, wherein the obtained compound is (−)-(2S,4aS,8aR)-5,5,8a-trimethyldecahydronaphthalen-2-yl acetate.

\* \* \* \* \*